United States Patent [19]

Friese et al.

[11] Patent Number: 5,662,786
[45] Date of Patent: Sep. 2, 1997

[54] ELECTROCHEMICAL SENSOR

[75] Inventors: Karl-Hermann Friese, Leonberg; Helmut Weyl, Schwieberdingen; Werner Wieland, Kornwestheim; Hans-Martin Wiedenmann, Stuttgart, all of Germany

[73] Assignee: Robert Bosch GmbH, Stuttgart, Germany

[21] Appl. No.: 807,163

[22] Filed: Dec. 13, 1991

Related U.S. Application Data

[63] Continuation-in-part of Ser. No. 372,363, Mar. 19, 1990, abandoned.

[51] Int. Cl.[6] .................................................. G01N 27/409
[52] U.S. Cl. ........................................... 204/429; 204/427
[58] Field of Search ................... 204/153.18, 421–429

[56] References Cited

U.S. PATENT DOCUMENTS

| | | | |
|---|---|---|---|
| 3,645,875 | 2/1972 | Record | 204/429 |
| 3,978,006 | 8/1976 | Topp et al. | 204/429 |
| 4,080,276 | 3/1978 | Bode | 204/429 |
| 4,121,988 | 10/1978 | Sano et al. | 204/429 |
| 4,164,462 | 8/1979 | Ichikawa et al. | 204/429 |
| 4,347,113 | 8/1982 | Fischer et al. | 204/428 |
| 4,359,374 | 11/1982 | Sano et al. | 204/429 |
| 4,502,939 | 3/1985 | Holfelder et al. | 204/426 |
| 4,879,016 | 11/1989 | Joshi | 204/421 |
| 4,947,125 | 8/1990 | De Pous | 204/424 |

FOREIGN PATENT DOCUMENTS 182642  10/1982  Japan .

*Primary Examiner*—T. Tung
*Attorney, Agent, or Firm*—Michael J. Striker

[57] ABSTRACT

The electrochemical sensor for determination of an oxygen content of exhaust gases, includes a probe element including a tube made from a raw material mixture consisting essentially of an ionically conductive solid electrolyte; an outer electrode located on the outer surface of the tube; a substantially pore-free conductor strip layer located on the outer surface, connected to the outer electrode, and extending toward the open end, the conductor strip layer having a portion in close proximity to the tube open end; and a substantially pore-free cover layer hermetically covering at least the portion of the pore-free conductor strip layer in close proximity to the open end of the tube, the cover layer being made from a cover layer material including the ionically conductive solid electrolyte. The cover layer material advantageously a sintering activity which is at least equal to that of the raw material mixture from which the tube is made. The conductor strip layer consists essentially of a ceramic supporting framework and an electron-conducting material. The ceramic ceramic binder has at least the same sintering activity as the cover layer material.

11 Claims, 1 Drawing Sheet

ELECTROCHEMICAL SENSOR

This application is a continuation-in-part application of U. S. patent application Ser. No. 07/372,363, filed Mar. 19, 1990, now abandoned.

BACKGROUND OF THE INVENTION

The present invention relates to an electrochemical sensor for determination of the oxygen content in exhaust gases.

It is generally known for determination of the oxygen content in exhaust gases, in particular in exhaust gases from an internal combustion engine, to use an electrochemical sensor.

Known sensors of this type are based on the principle of the oxygen concentration cell with an ionically conductive solid electrolyte acting as a probe element and having an inner and outer electrode. The probe element consists, for example, of a tube made of an ionically conductive solid electrolyte having an open end and a closed end. On the outer surface of the tube nearest to the open end there is an electrode which may consist, for example, of a porous platinum layer, which at the same time functions to bring about an adjustment to thermodynamic equilibrium. This adjustment of gas equilibrium is necessary, since the gas is generally not in thermodynamic equilibrium at the outset. This is a precondition for as sharp a jump in potential as possible at lambda =1 or, in the case of a polarographic limiting current probe (see German Patent 2,711,880), for the respective actual lambda value to be recorded.

The electrode layer, e.g. platinum layer, is very thin in the case of these sensors and, although it generally bears a porous ceramic protective layer, nevertheless, after prolonged use, it is subject to a corrosive attack by some of the constituents of the exhaust gas, e.g. soot, lead and phosphorous and sulfur compounds. This corrosive attack takes place over the entire area of the sensor tube, but is particularly strong in the vicinity of the open end of the tube, where, due to a lower temperature, these harmful constituents deposit more readily and do not revolatilize as readily and where the electrode layer is under certain circumstances no longer completely covered by the porous, and thus, in any case only, limitedly effective, protective layer.

To avoid the disadvantages mentioned of the known sensors, it is known from German Published Patent Application 2,619,746 to apply to the outer surface exposed to the exhaust gas of a solid electrolyte body forming the tube of the probe element an electron-conducting layer in the form of a conductor strip layer of a mixture of an electron-conducting material catalyzing the equilibration of the gas and, as needed, a ceramic material or glass, which acts as a supporting framework. This conductor strip layer extends from the closed end of the tube up to the open end. A glaze, instead of a porous ceramic cover layer of, for example, magnesium spinel or aluminum oxide, covers that portion of the conductor strip layer which is closest to the open end of the tube.

It has been found, however, that the covering of the conductor strip layer with a glaze, e.g. of potassium-aluminum silicate, barium-aluminum silicate or barium-calcium calcium-aluminum silicates, as described in German Published Patent Application 2,619,746, has a number of serious disadvantages. First, the glaze is applied only after the standard sintering process making additional work in the form of added process steps. Second, cracks readily form in this type of cover layer, so that the conductor strip layer is exposed to corrosive attack locally during operation of the sensor due to the very different material composition of the probe ceramic and thus the different thermal expansion.

SUMMARY OF THE INVENTION

It is an object of the present invention to provide an electrochemical sensor of the above-described type, which avoids the above-described disadvantages.

It is also an object of the present invention to provide an electrochemical sensor of the above-described kind, in which the conductor strip layer is hermetically covered by a cover layer in such a way that a fault-free operation of the sensor is possible, even in very rich exhaust gases at high temperatures.

According to our invention, the electrochemical sensor comprises a probe element. The probe element comprises a tube made from a raw material mixture consisting of an ionically conductive solid electrolyte, e.g. stabilized zirconium oxide. The tube has an open end, an outer surface and a closed end. An inner electrode is provided on the inner surface of the tube and an outer electrode is located on the outer surface. The outer surface is also provided with a conductor strip layer connected to the outer electrode extending from the outer electrode toward the open end of the tube. The conductor strip has a portion in close proximity to the open end of the tube, but does not necessarily extend to the end of the open end. A cover layer, which is substantially pore-free prior to sintering, hermetically covers the portion of the conductor strip layer in close proximity to and adjacent the open end of the probe element. The cover layer is made from a cover layer material including the ionically conductive solid electrolyte and having a sintering activity which is at least equal to that of the raw material mixture from which the tube is made. The conductor strip layer consists essentially of a ceramic binder and an electron-conducting material. The ceramic supporting framework, advantageously comprising a stabilized zirconium dioxide with a flux additive, has advantageously at least the same sintering activity as the raw material mixture of the tube. A fault-free continuous operation of the sensor is possible, even in very rich exhaust gases at high temperatures, because after a single sintering step both the cover layer and the conductor strip layer are substantially pore-free or nonporous.

The electrochemical sensor according to the invention with a compactly sintered cover layer of the raw material mixture from which the tube is made having the same or increased sintering activity has substantial advantages compared with the known sensors, e.g. of the type described in German Published Patent Application 2,619,746.

One major advantage of the invention is that the production of the sensor is simplified, since the cover layer can be applied to the conductor strip layer before the sintering process. Furthermore, the conductor strip layer is hermetically covered by the cover layer in such a way that a fault-free continuous operation of the sensor is possible even in very rich exhaust gases (lambda less than 0.8) at high temperatures with strong soot formation, since short circuits between conductor strip layer and housing can be avoided, i.e. the sensor signal cannot be confused with stray potentials introduced and corrosion of the conductor strip layer is reliably prevented by coating it with a nonporous cover layer.

The probe element, as a rule in the form of a finger, of the sensor according to the invention may consist of an ion-conducting solid electrolyte. The probe element can be, for example, made of stabilized zirconium dioxide, e.g. $ZrO_2$ stabilized with a stabilizer such as yttrium oxide or calcium oxide. Besides stabilized $ZrO_2$, the probe element may, however, also be made up of solid electrolytes based on $CeO_2$, $HfO_2$ or $ThO_2$, which may be stabilized, for example, with CaO, MgO, SrO, $Yb_2O_3$ and/or $Sc_2O_3$.

Consequently, if the probe element consists of, for example, $ZrO_2$ stabilized with 5 Mol % of yttrium oxide, stabilized $ZrO_2$ is also used for the cover layer. However the cover layer raw material should have at least the same sintering activity as the raw material out of which the tube itself is made.

The percentage composition of the raw material used to make the cover layer need not, however, correspond exactly to the composition of the probe element. All that is essential is that the same or equivalent raw materials are used. The percentage compositions may in fact deviate somewhat from each other. This means that the stabilizer content of the raw material mixture used for forming the cover layer may deviate by up to about 20% from the stabilizer content of the raw material mixture of the probe element.

A raw material mixture with increased sintering activity may also be used for producing the cover layer. An increased sintering activity is achieved, for example, by an intensified liberation and/or by addition of a siliceous flux, e.g. by addition of aluminum silicate, barium silicate or Ba-Al silicate. Such additives may be added to the raw material mixture, e.g., in quantities of approximately 5% by weight, based on the raw material mixture.

Cover layer materials from which the cover layer is made, e.g. spray suspensions or printing pastes, are advantageously composed as follows:

(a) 32 to 65% by weight of another solid electrolyte raw material mixture (Solid electrolyte oxide+stabilizer oxide+flux additives), (b) 1 to 8% by weight of an organic binder, and (c) 27 to 67% by weight of other additives such as solvents, anti-foaming agents, dispersion agents and set-up agents in known combinations.

Typical suitable organic binders are, e.g. polyvinyl butyral, acrylic resins and cellulose derivatives, e.g. ethyl cellulose.

Apart from water, organic solvents may also be employed for preparing the spray suspensions or printing pastes. The suspensions and pastes may be applied by usual application methods, e.g. spraying, rolling-on and printing.

The layer thickness of the cover layer produced is preferably from about 5 to 50 micrometers. Generally, it has proved particularly advantageous to adapt the layer thickness of the cover layer essentially to the conductor strip layer thickness, while not allowing the cover layer to become thinner than the conductor strip layer.

The conductor strip layer consists of the ceriamic binder and the electron-conducting materials. The electron-conducting materials usually employed for production of conductor strip layers, e.g. platinum, a platinum alloy, e.g. a platinum-rhodium alloy, or precious metal cermet e.g. a platinum cermet, may be used.

It is particularly advantageous that the conductor strip be a sinter-active ceramic binder, which makes possible the formation of a pore-free structure for the conductor strip layer materials suitable for forming sinter-active ceramic binder are, for example, stabilized zirconium dioxide powders. In one embodiment of the invention the conductor strip layer is about 60 to 80% by volume of a Pt/Rh alloy and about 40 to 20% by volume of a stabilized Zirconium dioxide powder.

By employing the cover layer and a Pt-cermet conductor strip layer with sinter-active ceramic binder a complete integration of the conductor strip layer in the probe element just below the probe element surface is possible. If appropriate, prior to application of the cover layer on the conductor strip layer, first an additional insulation layer, e.g. porously sintered aluminum oxide, may also be applied to the conductor strip layer, which layer ensures the electrical insulation of the conductor strip layer with respect to the probe housing even at elevated temperatures (>500° C.).

Generally the probe is made by applying the electrodes the conductor strip layer and the paste or the like used for the cover layer prior to sintering. Then the unsintered assembly is sintered forming a nonporous cover layer and conductor, strip layer in one step.

By "sintering activity" we mean the ability of a mixture to form a substantially nonporous solid on heating or sintering. Thus, a high sintering activity means that a nonporous solid is formed during sintering, but a low sintering activity means that a substantially porous solid is formed on heating or sintering.

BRIEF DESCRIPTION OF THE DRAWING

The objects, features and advantages of the present invention will now be illustrated in more detail by the following detailed description, reference being made to the accompanying drawing in which.

DETAILED DESCRIPTION OF THE INVENTION

Figure 1:
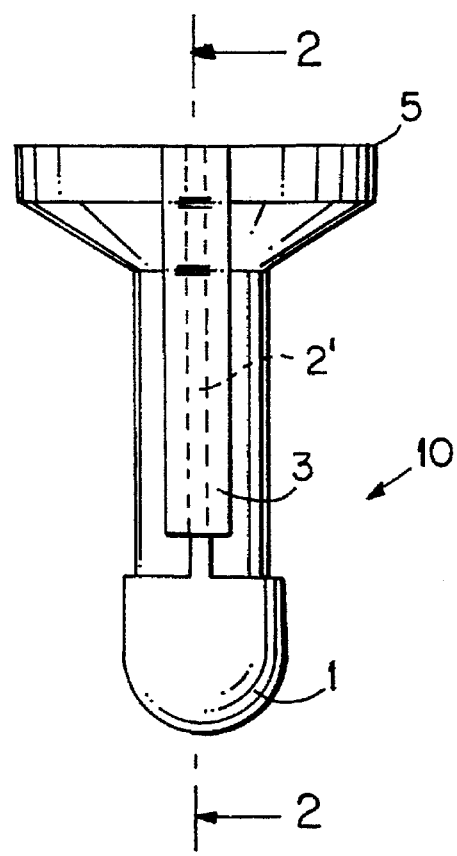
FIG. 1 is a side elevational view of an electrochemical sensor according to the invention.
Figure 2:
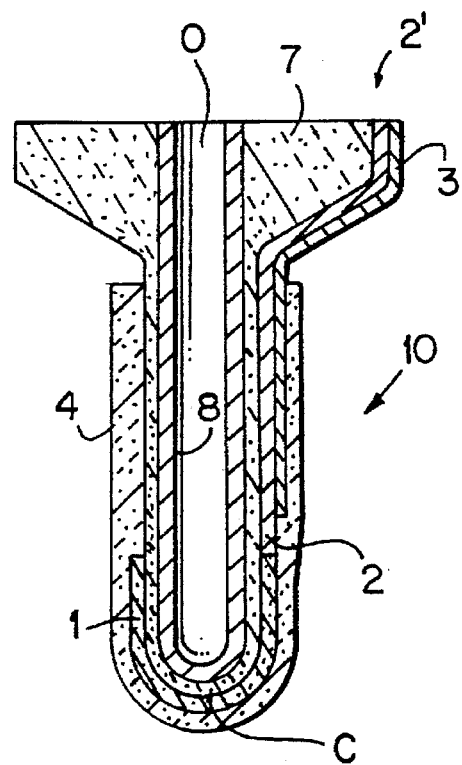
FIG. 2 is a longitudinal cross sectional view of the electrochemical sensor shown in FIG. 1.

An example of an electrochemical sensor according to the invention is shown in FIGS. 1 and 2.

The probe element 10 of the sensor includes a tube 7 made of a solid electrolyte as described above having a closed end C and an open end 0. A flange 5 is provided at the open end O of the tube 7. The inner electrode 8 is present on the interior surface of the tube. An outer electrode 1 is provided coating the closed end C of the tube 7. The outer electrode 1 is made of porous material. A porous protective layer 4 covers the closed end C of the tube and the outer electrode 1. Of course the layer 4 must be porous so that oxygen can reach the electrode 1.

The outer electrode 1 is connected to a substantially nonporous (after sintering) conductor track or strip 2 extending toward the open end of the tube 7 and in this case to the open end O. The conductor strip layer 2 has a portion 2' in close proximity to the open end O of the tube 7 which is covered hermetically by a substantially pore-free cover layer 3 without open porosity. Both the cover layer 3 and the conductor strip layer 2 are made from sinter-active raw material so that during manufacture which includes sintering, the protective cover layer 3 and the conductor strip layer 2 become substantially gas-tight and nonporous. That is what is meant by "hermetically covering". However another portion of the conductor strip layer 2 which extends to the closed end need not be covered.

While the invention has been illustrated and described as embodied in an electrochemical sensor, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is desired to be protected by Letters Patent is set forth in the appended claims.

We claim:

1. An electrochemical sensor for determination of an oxygen content of exhaust gases, comprising a probe element including a tube made from a raw material mixture consisting essentially of an ionically conductive solid electrolyte, said tube having an open end and a closed end and also having an outer surface, and an inner electrode; an outer electrode located on the outer surface; a substantially pore-free conductor strip layer located on the outer surface, connected to said outer electrode, and extending toward said open end from said outer electrode, the conductor strip layer having a portion in close proximity to the open end of the tube; and a substantially pore-free cover layer hermetically covering the portion of said conductor strip layer in close proximity to the open end of the tube, said cover layer being made from a cover layer material including the ionically conductive solid electrolyte, said cover layer material having a sintering activity which is at least equal to that of said raw material mixture from which said tube is made, said conductor strip layer consisting essentially of a ceramic binder and an electron-conducting material, said ceramic binder having at least the same sintering activity as that of said cover layer material.

2. An electrochemical sensor according to claim 1, wherein the cover layer has a layer thickness from about 5 to 50 micrometers.

3. An electrochemical sensor according to claim 2, wherein the layer thickness of the cover layer is not less than a conductor strip layer thickness.

4. An electrochemical sensor according to claim 1, wherein the cover layer material comprises stabilized $ZrO_2$.

5. An electrochemical sensor according to claim 1, wherein the cover layer material comprises stabilized $ZrO_2$ and a flux additive.

6. An electrochemical sensor according to claim 5, wherein said flux additive is an alkaline earth metal-aluminum oxide silicate.

7. An electrochemical sensor according to claim 6, wherein said substantially pore-free conductor strip layer is a cermet conductor strip layer.

8. An electrochemical sensor according to claim 7, wherein said ceramic binder of said conductor strip layer is made of zirconium dioxide having a sintering activity at least as large as said raw material mixture of said tube.

9. An electrochemical sensor according to claim 7, wherein said conductor strip layer is about 60 to 80% by volume of a Pt/Rh alloy and about 40 to 20% by volume of said ceramic binder, said ceramic binder being made of stabilized zirconium dioxide.

10. An electrochemical sensor according to claim 1, wherein said ionically conductive solid electrolyte from which said tube is made consists essentially of stabilized zirconium oxide, said stabilized zirconium oxide being stabilized with a stabilizer selected from the group consisting of yttrium oxide and calcium oxide.

11. An electrochemical sensor according to claim 1, wherein said ionically conductive solid electrolyte from which said tube is made consists essentially of a metal oxide selected from the group consisting of $CeO_2$, $HfO_2$, and $ThO_2$ stabilized with a stabilizer selected from the group consisting of CaO, MgO, SrO, $Yb_2O_3$ and $Sc_2O_3$.

* * * * *